(12) United States Patent
Kabata et al.

(10) Patent No.: US 8,486,716 B2
(45) Date of Patent: Jul. 16, 2013

(54) METHOD FOR DETECTION OF BASIC PEPTIDE AND REAGENT FOR DETECTION OF BASIC PEPTIDE

(75) Inventors: Hiroyuki Kabata, Kobe (JP); Hideki Takahashi, Kobe (JP); Ikuro Maruyama, Kagoshima (JP); Rena Tsuruoka, Kobe (JP)

(73) Assignees: Sysmex Corporation, Hyogo (JP); Kagoshima University, Kagoshima (JP)

( * ) Notice: Subject to any disclaimer, the term of this patent is extended or adjusted under 35 U.S.C. 154(b) by 0 days.

(21) Appl. No.: 13/491,296

(22) Filed: Jun. 7, 2012

(65) Prior Publication Data

US 2012/0244634 A1  Sep. 27, 2012

Related U.S. Application Data

(63) Continuation of application No. PCT/JP2010/072256, filed on Dec. 10, 2010.

(30) Foreign Application Priority Data

Dec. 10, 2009 (JP) .................. 2009-280935

(51) Int. Cl.
*G01N 33/52* (2006.01)
*G01N 33/53* (2006.01)
*C07K 14/77* (2006.01)

(52) U.S. Cl.
USPC ............. 436/501; 530/362; 530/363

(58) Field of Classification Search
None
See application file for complete search history.

(56) References Cited

PUBLICATIONS

Kaibara et al., Biomacromolecules 2000, 1, 100-107.*
(Huang et al., Proc. Natl. Acad. Sci. USA 1995; vol. 92, pp. 10312-10316.*
Aoki et al., Bull inst. Chem. Res., Kyoto Univ. 1969; vol. 47, No. 4, p. 274.*
Muramoto, Koji, et al., "Identification of the corticotrophin Binding Domain of Bovine Serum Albumin by Photoaffinity Labeling", Biochemistry, 1981, pp. 3380-3385, vol. 20.
Baczynskyj, Lubomyr, et al., "Application of Thermally Assisted Electrospray Ionization Mass Spectrometry for Detection of Noncovalent Complexes of Bovine Serum Albumin with Growth Hormone Releasing Factor and Other Biologically Active Peptides", Rapid Communications in Mass Spectrometry, 1994, pp. 280-286, vol. 8.
Dennis, Mark S., et al., "Albumin Binding as a General Strategy for Improving the Pharmacokinetics of Proteins", The Journal of Biological Chemistry, Sep. 20, 2002, pp. 35035-35043, vol. 277, No. 38.
Lowenthal, Mark S., et al., "Analysis of Albumin-Associated Peptides and Proteins from Ovarian Cancer Patients", Clinical Chemistry, 2005, pp. 1933-1945, vol. 51, No. 10.

* cited by examiner

*Primary Examiner* — Jacob Cheu
*Assistant Examiner* — Carmencita M Belei
(74) *Attorney, Agent, or Firm* — Sughrue Mion, PLLC

(57) ABSTRACT

The present invention provides a method for detection of a basic peptide by mixing a sample suspected to contain the basic peptide and a reagent containing denatured albumin and detecting turbidness due to a complex of the basic peptide and denatured albumin.

4 Claims, 9 Drawing Sheets

α — endorphin

METHOD FOR DETECTION OF BASIC PEPTIDE AND REAGENT FOR DETECTION OF BASIC PEPTIDE

CROSS-REFERENCE TO RELATED APPLICATION

This application is a continuation of International Application PCT/JP2010/072256 filed on Dec. 10, 2010, which claims benefit of Japanese patent application JP 2009-280935 filed on Dec. 10, 2009, both of which are incorporated herein by reference in their entireties.

BACKGROUND OF THE INVENTION

The present invention relates to a method for detection of a basic peptide. More specifically, the present invention relates to a method for detection of basic peptide by mixing a sample that potentially includes a basic peptide and a reagent that includes a denatured albumin and detecting the resultant turbidity due to a complex formation between the basic peptide and the denatured albumin. The present invention also relates to a reagent for detection of a basic peptide to be used for the method.

The concentrations in blood of certain basic peptides are known to alter depending on pathological conditions and show differences than those in a healthy normal state. To a group of such basic peptides typically belong ghrelin, brain natriuretic peptide (BNP), adrenocorticotrophic hormone (ACTH), atrial natriuretic peptide (ANP), bradykinin and like, and these peptides are regarded as useful disease markers in the field of clinical examination. For example, it has been known that the concentration of a basic peptide, ghrelin, observed in plasma from patients suffering from severe heart failure and those suffering gastric cancer with severe cachexia is decreased. The blood concentration of BNP is an important clinical index of heart failure and BNP is used as a marker for examination.

The basic peptides have been conventionally measured by immunological procedures such as enzyme immunoassay and electrochemiluminescence immunoassay. In these immunological procedures, the basic peptides are measured with antibodies that specifically recognize and bind to them. However, the procedures are complicated for these methods because a labeling substance needs to be attached to a complex of the antibody and the basic peptide in order to detect the complex.

On the other hand, Dennis et al. (Dennis M S et al., J. Biol. Chem. vol. 277, 35035-35043 (2002)) and Lowenthal et al. (Lowenthal M S et al., Clin. Chem. vol. 51, 1933-1945 (2005)) have reported non-immunological methods for detecting basic peptides in which the step for binding a labeling substance can be omitted. However, the methods reported require an expensive and large-scale mass spectrometer or surface plasmon resonance analyzer. Thus, the methods have remained to be widespread.

Dennis et al. and Lowenthal et al. have studied binding between naturally occurring albumin (non-denatured albumin) and basic peptides in order to discover pathological indexes, investigate pharmacological action and develop drug delivery systems.

Albumin is a protein naturally contained in, for example, egg white, serum or milk. For example, serum albumin is known to have physiological functions including regulation of blood osmotic pressure, and to circulate in blood after its binding to blood metabolites such as fatty acids, hematin or bilirubin, compounds such as drugs, or special peptides.

For example, Baczynskyj et al. (Baczynskyj L. et al., Rapid Commun. Mass Spectrom. vol. 8, 280-286 (1994)) have showed a possibility where a known blood hormone, bradykinin, bind to BSA. In addition, Muramoto et al. (Muramoto K. et al., Biochemistry. vol. 20, 3380-3385 (1981)) have reported that a blood hormone peptide, ACTH, binds to BSA.

SUMMARY OF THE INVENTION

The present inventors have investigated, in view of thermodynamic equilibrium, mechanisms of changes in molecular structure upon binding of a basic peptide to non-denatured albumin, particularly conferred with each other through their binding. The thermodynamic equilibrium is to describe the actual binding equilibrium among molecules in solution by definite values designated as a value of dissociation constant (Kd) representing extent of binding (lower or higher affinities) and a cooperativity (a value of Hill coefficient) reflecting allosteric structural changes upon binding.

Through the above study, the inventors have confirmed that basic peptides bind to non-denatured albumin as reported by Lowenthal et al. above. Detection by Lowenthal et al is based on mechanophysics and necessitates a mass spectrometer, where a mixture of a basic peptide and non-denatured albumin is once fixed on a polymer substrate for sample fixation of the mass spectrometer and then is developed. That is, in this detection method, both the basic peptide and non-denatured albumin never preserves the actual solution-based equilibrium and the method results in detection for only a biased population of molecules.

In striking contrast, the present inventors have maintained and ensured the basic peptide and non-denatured albumin in a solution persistently and then monitored the natural binding therebetween, namely the actual solution-based equilibrium. The present inventors have attempted to apply this form of equilibrium to creation of a method for detection of the basic peptide or the complex of the basic peptide and non-denatured albumin.

However, during the above investigation, the present inventors have elucidated that an affinity of binding between the basic peptide and non-denatured albumin is naturally weak, which has not been reported in the prior art. As a result, the sensitivity in detection is not sufficient in the above detection method.

Thus, in order to detect the complex, one candidate for the step is to utilize a labeling substance as mentioned above. The other is to design to enhance the affinity of binding in the form of the solution equilibrium.

One of the characteristics of the present invention is to meet the above needs. Thus, an object of the present invention is to provide a method which enables a convenient and rapid detection of basic peptides without the need of complicated procedures such as binding of a labeling substance. Another object of the present invention is to provide a reagent for detection of a basic peptide to be used in the detection method.

The present inventors have found that when a sample containing a basic peptide and a denatured bovine serum albumin solution are mixed, the mixture becomes turbid because of a complex formed between the denatured albumin and the basic peptide, and that the extent of the turbidity increases at higher concentrations of the basic peptide in the sample, thereby completing the present invention.

Thus, the present invention provides a method for detection of a basic peptide comprising the steps of:

(1) mixing a sample suspected to contain the basic peptide and a reagent containing denatured albumin to form a complex between the basic peptide and the denatured albumin; and (2) detecting a turbidness of a mixture obtained in the step (1).

The present invention further provides a reagent for detection of a basic peptide comprising denatured albumin.

According to the present invention, the method which allows convenient and rapid detection of basic peptides without the need of complicated steps such as binding of a labeling substance and the reagent to be used for the method are provided.

BRIEF DESCRIPTION OF THE DRAWINGS

FIG. 4-1 is a plot of varied concentrations of a peptide versus values of OD measured when α-endorphin is sought to be detect using the present reagent containing heat-denatured BSA;

FIG. 4-2 is a plot of varied concentrations of a peptide versus values of OD measured when a partial dynorphin A peptide is detected using the present reagent containing heat-denatured BSA;

FIG. 5-1 is a plot of varied concentrations of a peptide versus values of OD measured when a fragment from kininogen is detected using the present reagent containing heat-denatured BSA;

FIG. 5-2 is a plot of varied concentrations of a peptide versus values of OD measured when a fragment of ITIH4 is detected using the present reagent containing heat-denatured BSA;

FIG. 7-1 is a plot of varied concentrations of a peptide versus values of OD measured when Fibrinogen α is sought to be detected using the present reagent containing heat-denatured BSA;

FIG. 7-2 is a plot of varied concentrations of a peptide versus values of OD measured when C3f is sought to be detected using the present reagent containing heat-denatured BSA;

FIG. 7-3 is a plot of varied concentrations of a peptide versus values of OD measured when Factor XIII is sought to be detected using the present reagent containing heat-denatured BSA;

FIG. 7-4 is a plot of varied concentrations of a peptide versus values of OD measured in which the plots of FIG. 1 and FIGS. 7-1 to 7-3 are superimposed;

DETAILED DESCRIPTION OF THE EMBODIMENTS

Figure 1:
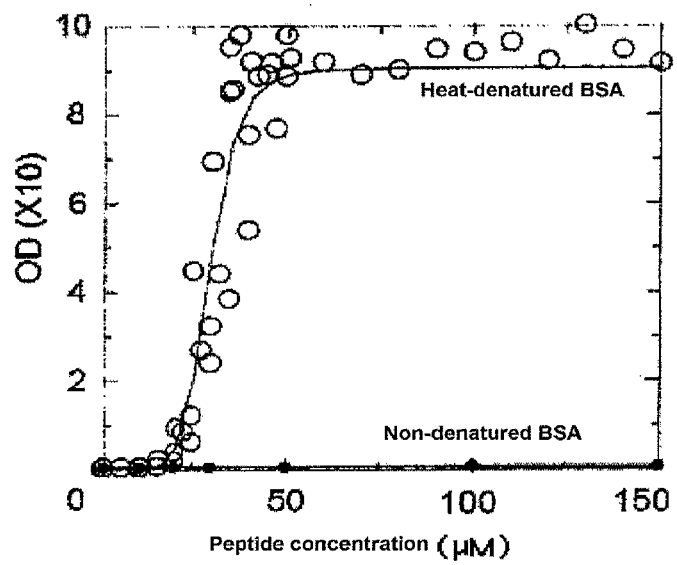
FIG. 1 is a plot of varied concentrations of a peptide versus values of OD measured when a partial ACTH peptide is detected using non-denatured BSA and the present reagent containing heat-denatured BSA.

The present method is the method for detection of a basic peptide comprising the following steps:

(1) mixing a sample suspected to contain the basic peptide and a reagent containing denatured albumin to form a complex between the basic peptide and the denatured albumin; and (2) detecting a turbidness of the mixture obtained in the step (1).

As used herein, "basic peptide" means a short chain peptide which has an isoelectric point (pI) within a basic range. Such a peptide preferably has a pI value of 8.0 or higher, and more preferably a pI value of 8.5 or higher, and preferably has a length of 10 to 100 amino acid residues, more preferably 10 to 60 amino acid residue length and still more preferably 10 to 40 amino acid residue length.

The intrinsic pI values of peptides can be experimentally measured with a well-known method in the art. When the amino acid sequence of a peptide is known, the pI value of the peptide can be theoretically estimated with an algorithm or program such as ExPASy proteomics server comput plotparam tool (available from expasy.ch/tools/protparam.html).

According to the present method, the basic peptide of interest is not specifically limited so long as it falls within the above definition and may be of natural origin or synthetic. The basic peptide of interest also includes basic peptides which are known to exist in specimens collected from living bodies with a specific pathological condition and show a difference in concentration than those for a healthy normal condition (e.g. ACTH, ANP, BNP, and ghrelin, and fragments of the following proteins: proto-oncogene protein L-myc-1, transcription factor SOX-3, fibrinogen α, inter-α-trypsin inhibitor heavy chain subunit 4 (ITIH4), α2-HS-glycoprotein, prothrombin and kininogen).

As used herein, "a sample suspected to contain a basic peptide of interest" means a sample which may potentially contain the basic peptide of interest. The sample may contain, for example, blood (including whole blood, plasma and serum), urine, saliva, biological tissue extract, spinal fluid, chest fluid, lymph fluid and the like.

The sample subjected to the detection according to the present method may contain contaminating substances (e.g. proteins and nucleic acids) other than the basic peptide of interest. However, for facilitating the detection, it is preferable to remove in advance the contaminating substances from the sample or to purify and/or concentrate beforehand the basic peptide of interest in the sample. The removal of contaminating substances and the purification and concentration of the basic peptide may be carried out with well-known methods in the art.

According to an embodiment of the present invention, for a case where the basic peptide in the sample containing high concentrations of salts is to be detected, the salts are preferably removed from the sample in advance. The removal of salts may be carried out with well-known methods in the art. According to the embodiment of the present invention, the salt concentration of the sample is preferably in a range of salt concentrations equivalent to 0 to 2 mS/cm of electric conductivity (e.g. 10 mM or less potassium phosphate buffer or 10 mM or less Tris-HCl), and more preferably in a range of salt concentrations equivalent to 0 to 160 μS/cm of electric conductivity (e.g. 900 μM or less potassium phosphate buffer).

As used herein, "albumin" has the same meaning as the term which is generally known in the art of biology, and collectively refers to a group of soluble proteins contained in body fluid and cells of animals and plants.

The known albumins of animal origin include serum albumin contained in serum, ovoalbumin contained in egg white, lactoalbumin contained in milk and the like. The known albumins of plant origin includes include leucosin contained in wheat and barley, legumelin contained in seeds of garden peas and soybeans, ricin contained in seeds of castor-oil plant and the like.

According to an embodiment of the present invention, the reagent is used which contains preferably albumin of animal origin, more preferably serum albumin, ovoalbumin or lactoalbumin, and still more preferably denatured albumin originated from serum albumin.

As used herein, "denatured albumin" means albumin whose conformation intrinsic to a physiological condition is perturbed due to a physical or chemical action. The physical cause may include, for example, treatment by heating, pressurization, freezing, ultrasonication or the like. The chemical cause may include treatment with a denaturing agent such as a surfactant including SDS, urea, guanidine hydrochloride or the like.

According to an embodiment of the present invention, the reagent is used which contains albumin denatured by the above treatment, and preferably heat-denatured albumin.

In the step (1) of the present method, a sample suspected to contain a basic peptide of interest and a reagent containing denatured albumin are mixed to form a complex of the basic peptide and denatured albumin.

More specifically, the reagent containing denatured albumin and the sample are mixed so as to adjust a final concentration of denatured albumin in the mixed solution of the reagent and the sample to 0.2 to 0.6 w/v %, and preferably 0.2 w/v %. This step of mixing is preferably carried out at 4 to 50° C., and more preferably 10 to 40° C.

By mixing the reagent and the sample, denatured albumin binds to the basic peptide to form complexes. These complexes are further aggregated to make the mixed solution turbid.

In the step (2) of the present method, the turbidness of the mixed solution obtained in the above step (1) is then detected.

As used herein, "to detect a turbidness" is intended to include detection of presence or absence of a turbidness of the mixed solution and measurement of extent of turbidness (hereinafter referred to as "turbidity"). Detection of presence or absence of turbidness can be carried out by visual observation with naked eye or a microscope, or with a turbidimeter. Measurement of turbidity can be carried out with a turbidimeter.

In the present method, turbidness upon the complex formation of denatured albumin and the basic peptide is detected; thus the method does not require a labeling substance or an antibody, unlike conventional methods, and enables detection of the basic protein only with the reagent containing denatured albumin.

Turbidity can be measured by irradiating the mixed solution with light and obtaining optical information. The optical information may include, for example, absorbance, scattered light intensity, reflected light intensity, diffracted light intensity, fluorescence intensity, phosphorescence intensity, polarization state, refractive index, optical rotatory and the like. Among these, absorbance is preferred as it can be measured with a simple apparatus. The apparatus for absorbance measurement may include, for example, a spectrophotometer UV-2500PC (Shimadzu Corporation). The turbidity is preferably measured by visible light at a wavelength of 400 to 700 nm and more preferably at a wavelength of 500 to 600 nm.

According to the present method, the concentration of the basic peptide of interest in the sample can be quantified based on the measured value of the turbidity. The concentration can be determined by referring to a calibration curve prepared with solutions of the basic peptide of interest having known concentrations.

The calibration curve may be prepared as follows. Solutions of the basic peptide of interest having various concentrations are first prepared (hereinafter referred to as "samples for calibration curve preparation"). The samples for calibration curve preparation are then mixed with the reagent containing denatured albumin and the turbidities of the obtained mixed solutions are measured. The measured values for the respective samples for calibration curve preparation are plotted on the vertical axis against the concentrations of the basic peptide on the horizontal axis. The samples for calibration curve preparation are respectively prepared to present gradually increasing peptide concentrations up to a maximum giving a plateauing value of turbidity from a solution without the basic peptide of interest.

It has been now found that the relationship between the measured values of turbidity and the concentrations of the basic peptide is governed by the following Hill equation (I). Thus, a calibration curve can be produced by obtaining the formula (I) or a linearization equation of (II) as follows by logarithmically transforming both side of the equation (I).

$$\text{Hill equation: } \theta = C^n/(C^n + Kd^n) \tag{I}$$

$$\text{Linearization equation: } \log\{\theta/(1-\theta)\} = n \log C - n \log Kd \tag{II}$$

(wherein θ represents a measured turbidity value, C represents a concentration of a basic peptide, Kd represents a dissociation constant, and n represents the Hill coefficient).

As used herein, the dissociation constant means the concentration of the basic peptide of interest at which 50% of the basic peptide is saturated by denatured albumin.

As used herein, the Hill coefficient is a characteristic index for cooperativity in binding of the basic peptide of interest to the denatured albumin (formation of a complex). In the case of a Hill coefficient of higher than 1, their complex formation is positively cooperative through an allosteric effect, and when the concentration of the basic peptide is increased, binding of the peptide to denatured albumin is promoted.

The Kd and n values can be calculated respectively from the concentration of the basic peptide in the samples for calibration curve preparation and from the measured values of turbidity.

Because the above equations (I) and (II) are a function of the measured turbidity value and the concentration of the basic peptide, the concentration of the basic peptide in a sample suspected to contain the basic peptide of interest can be quantified from the measured turbidity value of the sample using the prepared calibration curve.

Elucidation of the complete mechanism is underway where turbidness is generated by mixing denatured albumin and the basic peptide. However, the followings may be contemplated.

First of all, the binding and the consecutive complex formation of denatured albumin and a basic peptide is mainly governed by an electrostatic interaction between the denatured albumin and the positive charges of the basic peptide. The complexes are then aggregated to produce turbid.

It is believed that the manner of the binding is ionic binding. This may also be suggested by the fact that the detection of the basic peptide in the present method is facilitated under low salt concentration conditions. It is believed that under low salt concentration conditions, ionic binding between denatured albumin and the basic peptide is promoted due to a decreased amount of ions.

It is believed that if the binding between denatured albumin and the basic peptide of interest is ionic binding, the binding does not depend on the amino acid sequence and the conformation of the peptide. Thus, it is contemplated that the present method is widely used for detection of various basic peptides.

The present method is advantageous because turbidness due to the formation of the complex between denatured albumin and the basic peptide appears immediately (e.g. 20 seconds or less, preferably instantly) after mixing the reagent containing denatured albumin and a sample containing the basic peptide.

Therefore, the present method enables a rapid detection of the basic peptide in a sample.

Because the present method enables detection of a basic peptide which is a disease marker in a biological specimen, it can be utilized as a method for diagnosis of a specific disease. In a situation where a sample solution is blood collected from a medical examinee, the basic peptide of interest which is particularly selected as a disease marker is purified and/or concentrated from the blood, the concentration of the peptide is then measured by the present method, and the obtained value is compared with the value at a healthy normal state, thereby diagnosing whether or not the he/she suffers from the disease.

The "reagent containing denatured albumin" used in the above present method also constitutes the present invention. Thus, the present reagent is the reagent for detection of a basic peptide containing denatured albumin.

The present reagent can be obtained as follows. Albumin of animal origin, preferably serum albumin, ovoalbumin or lactoalbumin or a mixture thereof, more preferably serum albumin is first dissolved in an appropriate solvent to prepare an albumin solution. The concentration of albumin in the solution is 0.2 to 5.0 w/v % and preferably 0.2 to 0.6 w/v %.

The solvent is not specifically limited so long as it does not prevent the formation of the complex between denatured albumin and the basic peptide, and may include, for example, ultrapure water and buffers such as 10 mM Tris-HCl (pH 5.5 to 7.5) and 10 mM potassium phosphate buffer (pH 5.5 to 7.5). Among these, ultrapure water is preferred. As used herein, "ultrapure water" means water having a specific resistance at 25° C. of 18 MΩ·cm or higher. Such ultrapure water is preferably Milli-Q® water.

The obtained albumin solution is then subjected to physical or chemical denaturing treatment. The physical denaturing treatment includes, for example, heating, pressurization, freezing, ultrasonication and the like. The chemical denaturing treatment includes treatment with a denaturing agent such as a surfactant including SDS, urea, guanidine hydrochloride or a mixture thereof.

For example, the albumin solution may be heated at a temperature of 100 to 130° C., preferably 110 to 120° C. for 5 to 120 minutes, preferably 10 to 60 minutes in heat treatment.

For example, the albumin solution may be added and mixed with SDS (final concentration: 1 to 30 w/v %) and urea (final concentration: 500 mM to 5M) in denaturation using a mixture of SDS and urea.

The present reagent preferably contains heat-denatured albumin or albumin denatured with a mixture of SDS and urea, more preferably heat-denatured albumin. The present reagent is preferably in the form of a solution.

It is believed that when the present reagent obtained as above is mixed with a sample containing the basic peptide, a complex is formed through ionic binding of denatured albumin and the basic peptide. The relation between the turbidity due to the complex and the concentration of the basic peptide is found to follow the above Hill equation (I).

Thus, although the detailed structure of denatured albumin contained in the present reagent remains to be solved fully, it is suggested that the denatured albumin contained in the present reagent is an allosteric protein having a plurality of sites electrostatistically binding to the basic peptide and possessing domains for binding to basic peptides in a positive cooperative fashion.

The present reagent preferably contains denatured albumin which binds to the basic peptide having an amino acid sequence SEQ ID NO: 1 with the dissociation constant of 5 to 220 μM.

The present reagent preferably contains denatured albumin which binds to the basic peptide having an amino acid sequence SEQ ID NO: 1 with the Hill coefficient of higher than 1 and lower than 11.

The dissociation constant and the Hill coefficient can be determined from the Hill equation (I) when the measured turbidity value and the concentration of the basic peptide are known. The amino acid sequence SEQ ID NO: 1 is the partial sequence of ACTH corresponding to position 1 to position 24 from the N-terminus.

The present invention is now described by means of examples which do not limit the present invention.

EXAMPLES

Example 1

Detection of Basic Peptide with Denatured or Non-Denatured BSA

1. Experimental Procedures
(1) Preparation of Solution of Denatured or Non-Denatured BSA as Reagent for Detection BSA (Sigma-Aldrich) was dissolved in Milli-Q® water (Millipore) to prepare a BSA solution (1.0 w/v %). The BSA solution was divided into two and one was designated as a non-denatured BSA solution and the other was autoclaved at 110° C. for 15 minutes to obtain a heat-denatured BSA solution.

(2) Preparation of Sample Containing Basic Peptide of Interest

A partial ACTH peptide (Peptide Institute, Inc.) consisting of the amino acids of positions 1 to 24 of ACTH was used as the basic peptide of interest. The peptide was dissolved in ultrapure water to prepare a sample containing the basic peptide of interest (1.0 mg/ml).

(3) Preparation of Mixed Solution of Reagent for Detection and Sample

The heat-denatured BSA solution prepared in the above (1) (50 μl) was mixed with the sample prepared in (2) followed by addition of ultrapure water to prepare a total volume of 250 μl of a mixed solution (final concentration of heat-denatured BSA: 0.2 w/v %). In this preparation, the sample was mixed so as to obtain a final concentration of the partial ACTH peptide in the mixed solution of 0 to 150 μM. A comparative mixed solution was also prepared in the similar manner except that the non-denatured BSA solution was used instead of the heat-denatured BSA solution.

(4) Measurement of Absorbance of Mixed Solution

The thus-prepared mixed solutions were measured for absorbance at the wavelength of 550 nm (OD550) in a spectrophotometer UV-2500PC (Shimadzu Corporation). The results are shown in FIG. 1. The obtained results were subjected to Hill plot analysis with KaleidaGraph (HULINKS, Inc.) to calculate the values of Kd and the Hill coefficient of heat-denatured BSA and non-denatured BSA. The values are shown in Table 1.

TABLE 1

| Reagent | Kd (µM) | Hill coefficient n |
|---|---|---|
| Heat-denatured BSA | 30 | 8 |
| Non-denatured BSA | 290 | 1 |

2. Results

According to FIG. 1, it was found that significant change in the value of OD550 was not observed when the non-denatured BSA solution was used. This means rapid dissociation of ACTH from non-denatured BSA after their binding or a poor production of turbidness even after binding.

On the other hand, the value of OD550 was increased in a concentration dependent manner of the basic peptide when the heat-denatured BSA solution was used. In this case of using heat-denatured BSA solution, the relationship following the Hill equation as follows could be recognized between absorbance and the basic peptide concentration.

$$OD = (\text{basic peptide concentration})^n / \{(\text{basic peptide concentration})^n + Kd^n\}$$

The comparison between Kd values of heat-denatured BSA and non-denatured BSA revealed that the value for heat-denatured BSA was smaller. From this fact, it was found that heat-denatured BSA possesses an extremely higher affinity for the basic peptide, ACTH, than non-denatured BSA.

The comparison between Hill coefficients of heat-denatured BSA and non-denatured BSA revealed that the Hill coefficient of non-denatured BSA was 1, while that of heat-denatured BSA was 8. When the Hill coefficient is higher than 1, it means it has a positive cooperativity (allosteric effect) and when the coefficient is 1, it means that it does not have cooperativity. Namely, due to the absence of cooperativity between non-denatured BSA and ACTH, they bind irrespective of the ACTH concentration in the mixture.

On the other hand, due to the presence of positive cooperativity between binding of heat-denatured BSA and ACTH, binding between heat-denatured BSA and ACTH is promoted when the ACTH concentration is increased.

Thus, denatured albumin can represent a slight change of the concentration of the basic peptide as the change in absorbance. Therefore, it is found that the present method can be used for detection and quantification of the concentration of the basic peptide.

Example 2

Investigation of Period for Heat Denaturation of BSA

1. Experimental Procedures
(1) Preparation of Denatured BSA Solutions with Various Heat Denaturation Periods BSA (Sigma-Aldrich) was dissolved in Milli-Q® water (Millipore) to prepare a BSA solution (1.0 w/v %). The BSA solution was divided into five aliquots among which one was designated as a non-denatured BSA solution (heat denaturation period: 0 min) and the rest of four were heated in an autoclave at 110° C. for 5, 15, 60 and 120 min, respectively, to obtain heat-denatured BSA solutions.

(2) Preparation of Sample Containing Basic Peptide of Interest

A partial ACTH peptide (Peptide Institute, Inc.) consisting of the amino acids of positions 1 to 24 of ACTH was used as the basic peptide of interest. The peptide was dissolved in ultrapure water to prepare a sample containing the basic peptide of interest (1.0 mg/ml).

(3) Preparation of Mixed Solutions of Denatured BSA Solutions with Respective Heat Denaturation Periods and Sample The denatured BSA solutions with respective heat denaturation periods prepared in the above (1) and the sample prepared in the above (2) were used to prepare mixed solutions in the similar manner as Example 1.

(4) Measurement of Absorbance of Mixed Solutions

Figure 2:
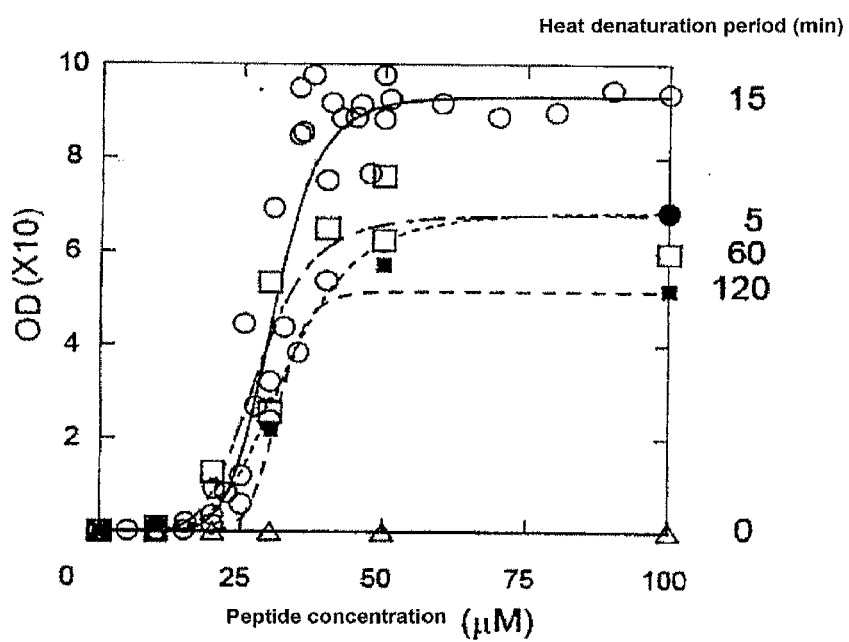
FIG. 2 is a plot of varied concentrations of a peptide versus values of OD measured when a partial ACTH peptide is detected using the reagent, for which BSA in the reagent was heated to be denatured for 0, 5, 15, 60 and 120 minutes.

The thus-prepared mixed solutions were measured for OD550 in the similar manner as Example 1. The results are shown in FIG. 2. The Kd value and Hill coefficient of BSA at respective heat denaturation periods were calculated. The values are shown in Table 2.

TABLE 2

| Heat denaturation period (min) | Kd (µM) | Hill coefficient n |
|---|---|---|
| 0 | 290 | 1 |
| 5 | 33 | 5 |
| 15 | 30 | 8 |
| 60 | 28 | 6 |
| 120 | 33 | 4 |

2. Results

According to FIG. 2, it is found that OD550 was not changed when the BSA solution that was heat-denatured for 0 min was used. The other BSA solutions that were heat-denatured for 5, 15, 60 and 120 minutes respectively showed that each of OD550 increased in a concentration dependent manner of the basic peptide.

Table 2 shows that the BSA solution heat-denatured for 0 minutes had a high Kd value, while the BSA solutions heat-denatured for 5, 15, 60 and 120 minutes had low Kd values. The Hill coefficient of the BSA solution heat-denatured for 0 minutes was 1, while those of the BSA solutions heat-denatured for 5, 15, 60 and 120 minutes were in the range of 4 to 8.

On the other hand, comparison between the BSA solutions heat-denatured for 5, 15, 60 and 120 minutes showed insignificant difference in both Kd values and Hill coefficients. It is thus found that the heat-denatured BSA solutions had similar affinity and positive cooperativity towards the partial ACTH peptide regardless of the heat denaturation period.

Example 3

Evaluation of Effects of Nucleic Acid on Detection of Basic Peptide

1. Experimental Procedures
(1) Preparation of Solution of Denatured BSA as Reagent for Detection The heat-denatured BSA solution was prepared in the similar manner as Example 1.

(2) Preparation of Sample Containing Basic Peptide of Interest

A partial ACTH peptide (Peptide Institute, Inc.) consisting of amino acids of positions 1 to 24 of ACTH was used as the basic peptide of interest. The peptide was dissolved in ultrapure water to prepare a sample containing the basic peptide of interest (1.0 mg/ml).

(3) Preparation of Mixed Solution of Reagent for Detection and Sample

The denatured BSA solution with respective heat denaturation periods prepared in the above (1) and the sample prepared in the above (2) were used to prepare mixed solutions in the similar manner as Example 1. A comparative mixed solution was prepared by adding to the mixed solution a salmon sperm DNA (trade name: Sonicated Salmon Sperm DNA, BioDynamics Laboratory Inc.) as nucleic acid (final concentration of nucleic acid: 10 µM).

(4) Measurement of Absorbance of Mixed Solution

Figure 3:
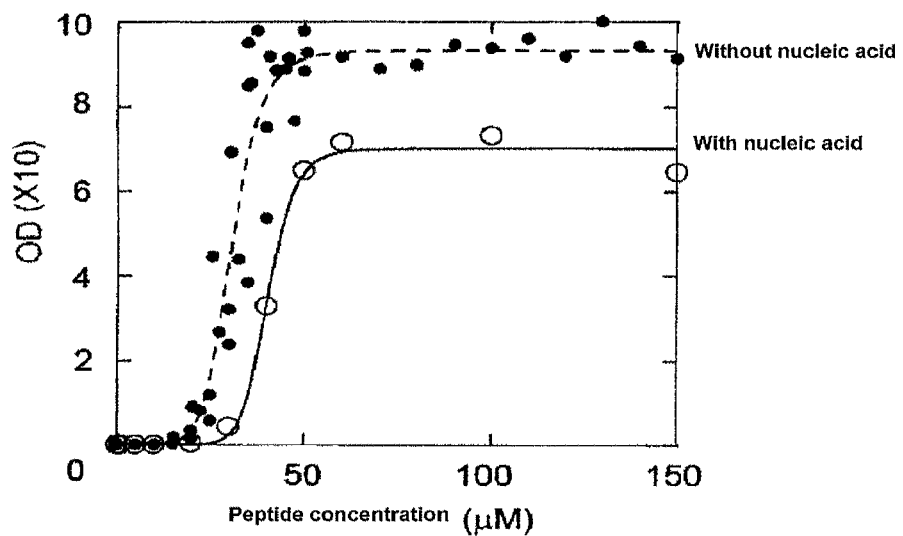
FIG. 3 is a plot of varied concentrations of a peptide versus values of OD measured when a partial ACTH peptide is detected in a sample with or without nucleic acid using the present reagent containing heat-denatured BSA.

The thus-prepared mixed solutions were measured for OD550 in the similar manner as Example 1. The results are shown in FIG. 3. The Kd value and Hill coefficient were calculated for the mixed solutions. The values are shown in Table 3.

TABLE 3

| Nucleic acid | Kd (µM) | Hill coefficient n |
|---|---|---|
| Yes | 30 | 8 |
| No | 40 | 11 |

2. Results

FIG. 3 shows that OD550 was increased in a concentration dependent manner of the basic peptide when the mixed solution contained nucleic acid, similar to the mixed solution without nucleic acid. Table 3 also shows that the calculated values of Kd and Hill coefficient are not significantly different between the mixed solutions with and without nucleic acid.

Thus, it is found that the present method for detection of a basic peptide is not significantly affected by the presence of nucleic acid in the sample.

Example 4

Detection of Basic Peptide and Neutral Peptide

1. Experimental Procedures (1) Preparation of Solution of Denatured BSA as Reagent for Detection The heat-denatured BSA solution was prepared in the similar manner as Example 1.

(2) Preparation of Sample Containing Basic Peptide of Interest

A partial dynorphin A peptide consisting of amino acids of positions 1 to 13 of dynorphin A (SEQ ID NO: 2; Peptide Institute, Inc.) was used as the basic peptide of interest. A neutral peptide, α-endorphin (SEQ ID NO: 3; Peptide Institute, Inc.) was also used as a comparative peptide of interest. These peptides were dissolved in ultrapure water to prepare samples containing respective peptides (1.0 mg/ml).

(3) Preparation of Mixed Solution of Reagent for Detection and Sample

The denatured BSA solution prepared in the above (1) (50 µl) was mixed with the respective samples prepared in (2) followed by addition of ultrapure water to prepare a total volume of 250 µl of mixed solutions containing respective peptides. In the preparation, the sample was mixed so as to obtain a final concentration of the respective peptides in the mixed solutions of 0 to 150 µM.

(4) Measurement of Absorbance of Mixed Solution

Figures 1, 4:
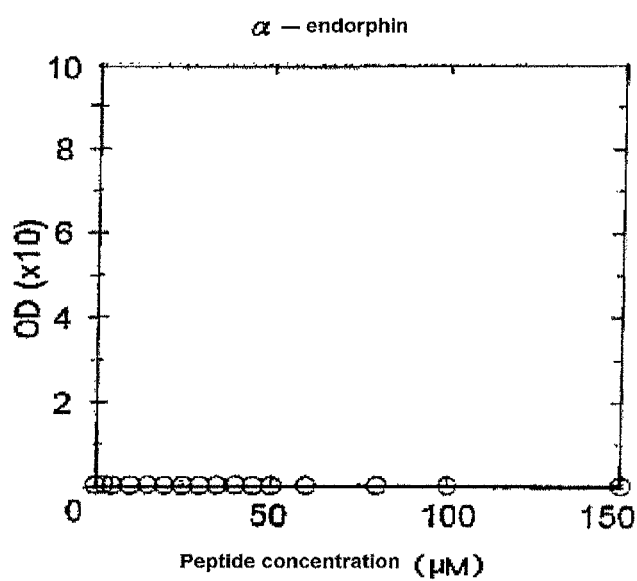
Figures 2, 4:
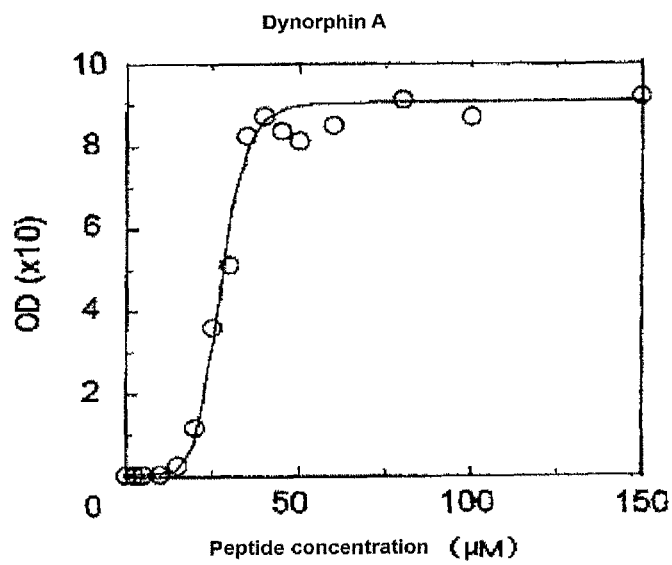

The thus-prepared mixed solutions were measured for OD550 in the similar manner as Example 1. The results are shown in FIG. 4. The obtained values of Kd and Hill coefficient of the sample containing the partial dynorphin A peptide were 30 and 8, respectively.

2. Results

There was no change in OD550 for the neutral peptide, α-endorphin (see FIG. 4-1). This may be because that heat-denatured BSA did not bind to α-endorphin or because the BSA dissociated from the peptide immediately after binding.

On the other hand, the value of OD550 was increased in a concentration dependent manner of the basic peptide, the partial dynorphin A peptide (see FIG. 4-2).

The obtained Kd value shows that the heat-denatured BSA showed a high affinity for the basic peptide, dynorphin A. In addition, binding of the heat-denatured BSA to dynorphin A showed the Hill coefficient of 8, and positive cooperativity.

Consequently, the present method can be specifically utilized for detection of the presence of and determination of concentration of the basic peptide.

Example 5

Detection of Basic Peptide, as Cancer Metastasis Marker

1. Experimental Procedures (1) Preparation of Solution of Denatured BSA as Reagent for Detection The heat-denatured BSA solution was prepared in the similar manner as Example 1.

(2) Preparation of Sample Containing Basic Peptide of Interest

A fragment of kininogen (positions 439 to 457 (SEQ ID NO: 4); synthesized at Biologica Co.) and a fragment of ITIH4 (positions 611 to 642 (SEQ ID NO: 5); synthesized at Biologica Co.) which were known as cancer metastasis markers were used as basic peptides of interest. These peptides were dissolved in ultrapure water to prepare samples containing respective peptides (1.0 mg/ml).

(3) Preparation of Mixed Solution of Reagent for Detection and Sample

The denatured BSA solution prepared in the above (1) (500) was mixed with the respective samples prepared in (2) followed by addition of ultrapure water to prepare a total volume of 250 µl of mixed solutions containing respective peptides. In the preparation, the sample was mixed so as to obtain a final concentration of the respective peptides in the mixed solutions of 0 to 80 µM.

(4) Measurement of Absorbance of Mixed Solution

Figures 1, 5:
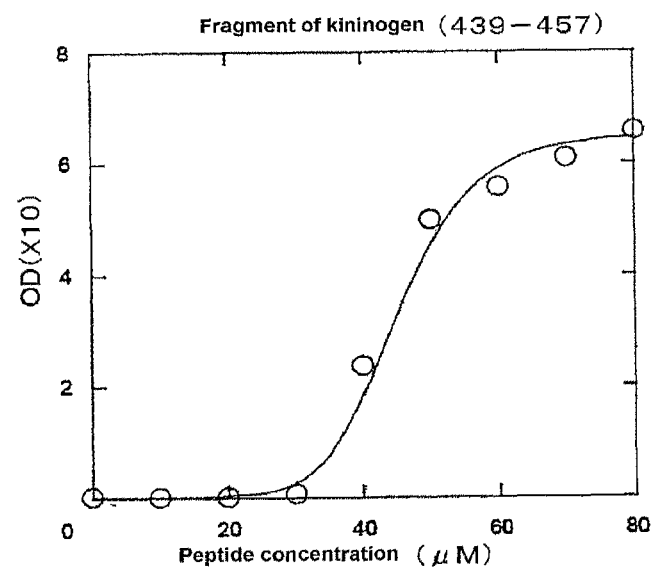
Figures 2, 5:
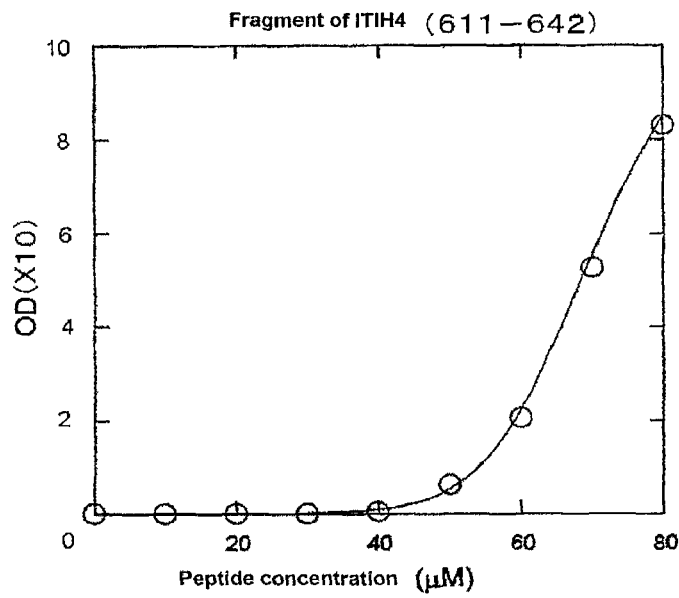

The thus-prepared mixed solutions were measured for OD550 in the similar manner as Example 1. The results are shown in FIGS. 5-1 and 5-2. The Kd value and Hill coefficient were calculated for the respective samples. The values are shown in Table 4.

TABLE 4

| Basic peptide | Kd (µM) | Hill coefficient n |
|---|---|---|
| Kininogen (439-457) | 45 | 8 |
| ITIH4 (611-642) | 70 | 9 |

2. Results

The measured OD550 value increased, as the concentration of the kiniongen fragment in the sample increased (see FIG. 5-1). From the Kd value and Hill coefficient, it is found that heat-denatured BSA binds to the kininogen fragment with a high affinity and a positive cooperativity.

Similarly, for the case of the ITIH4 fragment, the measured value of OD550 increased in a peptide concentration dependent manner (see FIG. 5-2). From the Kd value and Hill coefficient, it is found that heat-denatured BSA binds to the ITIH4 fragment with a high affinity and a positive cooperativity.

Thus, the present method can be utilized for detection of the presence of and quantification of the concentration of the basic peptid, as the cancer marker.

Example 6

Detection of Basic Peptide with Heat-Denatured Human Serum Albumin (HSA) and Heat-Denatured Ovoalbumin (OA)

Figure 6:
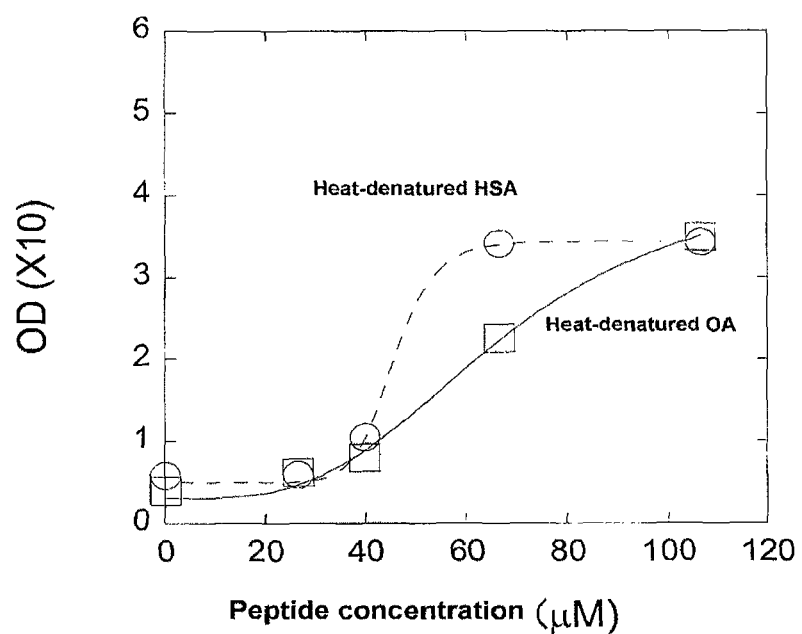
FIG. 6 is a plot of varied concentrations of a peptide versus values of OD measured when a partial ACTH peptide is detected using the present reagent containing either of heat-denatured human serum albumin (HSA) and heat-denatured ovoalbumin (OA)

1. Experimental Procedures
(1) Preparation of Solution of Denatured HSA and Solution of Denatured OA as Reagents for Detection HSA (Wako Pure Chemicals) was dissolved in ultrapure water to prepare a HSA solution (1.0 w/v %). The HSA solution was heated in an autoclave at 115° C. for 15 minutes to prepare a heat-denatured HSA solution. OA (Worthington) was also dissolved in ultrapure water to prepare an OA solution (1.0 w/v %). The OA solution was adjusted its pH to 5 to 7 with sodium hydroxide and autoclaved at 115° C. for 15 minutes to prepare a heat-denatured OA solution.
(2) Preparation of Sample Containing Basic Peptide of Interest A partial ACTH peptide consisting of amino acids of positions 1 to 24 of ACTH (Biologica Co.) was used as the basic peptide of interest. The peptide was dissolved in ultrapure water to prepare a sample containing the basic peptide of interest (1.0 mg/ml).
(3) Preparation of Mixed Solution of Reagent for Detection and Sample The heat-denatured HSA solution prepared in the above (1) (50 μl) was mixed with the sample prepared in (2) followed by addition of ultrapure water to prepare a total volume of 250 μl of a mixed solution (final concentration of heat-denatured HSA: 0.2 w/v %). In the preparation, the sample was mixed so as to obtain a final concentration of the partial ACTH peptide in the mixed solution of 0 to 80 μM. A mixed solution was also prepared in the similar manner except that the heat-denatured OA solution was used instead of the heat-denatured HSA solution (final concentration of heat-denatured OA: 0.2 w/v %).
(4) Measurement of Absorbance of Mixed Solution The thus-prepared mixed solutions were measured for absorbance at the wavelength of 550 nm (OD550) with a spectrophotometer UV-2500PC (Shimadzu Corporation). The results are shown in FIG. 6. The obtained results were subjected to Hill plot analysis with KaleidaGraph (HULINKS, Inc.) to calculate Kd and the Hill coefficient values of heat-denatured HSA and heat-denatured OA. The values are shown in Table 5.

TABLE 5

| Reagent | Kd (μM) | Hill coefficient n |
|---|---|---|
| Heat-denatured HSA | 46 | 11 |
| Heat-denatured OA | 67 | 3 |

Results

From FIG. 6, both of the heat-denatured HSA solution and the heat-denatured OA solution enabled the value of OD550 to increase in a manner dependent on the concentrations of the basic peptide. Table 5 shows that the Kd values were relatively low and the Hill coefficient values were 3 and 11, respectively. These indicate that both reagents of heat-denatured HSA and OA had affinity and positive cooperativity towards the partial ACTH peptide.

These facts indicate that the reagents containing denatured HSA and OA are able to be used to detect and quantify the concentration of the basic peptide.

Example 7

Investigation of Optimal Concentration of Reagent for Detection in Detection of Peptides 1. Experimental Procedures
(1) Preparation of Solution of Denatured BSA as Reagent for Detection BSA (Sigma-Aldrich) was dissolved in ultrapure water to prepare a BSA solution (5.0 w/v %). The BSA solution was heated in an autoclave at 115° C. for 15 minutes to obtain a heat-denatured BSA solution.
(2) Preparation of Sample Containing Basic Peptide of Interest A partial ACTH peptide consisting of amino acids of positions 1 to 24 of ACTH (Biologica Co.) was used as the basic peptide of interest. The peptide was dissolved in ultrapure water to prepare a sample containing the basic peptide of interest (1.0 mg/ml).
(3) Preparation of Mixed Solution of Reagent for Detection and Sample The heat-denatured BSA solution prepared in (1) was mixed with 30 μl or 60 μl of the sample prepared in (2) followed by addition of ultrapure water to prepare a total volume of 250 μl of mixed solutions. In the preparation, the reagent for detection (solution of heat-denatured BSA) was mixed with the respective samples so as to obtain a final concentration of the reagent for detection in the mixed solution of 0.1 to 5%.
(4) Evaluation of Turbidity of Mixed Solution The thus-prepared mixed solutions were measured for values of absorbance at the wavelength of 550 nm (OD550) with a spectrophotometer UV-2500PC (Shimadzu Corporation). The results obtained are summarized in Table 6, where "Y" denotes turbidity appearing and "N" does the absence of turbidity.

TABLE 6

| Final conc. of reagent (%) | Detection capacity (in the case of 30 μM peptide) | Detection capacity (in the case of 60 μM peptide) |
|---|---|---|
| 0.1 | Y | Y |
| 0.2 | Y | Y |
| 0.4 | Y | Y |
| 0.5 | Y | Y |
| 0.7 | Y | Y |
| 1.0 | Y | Y |
| 5.0 | Y | Y |

2. Results

From Table 6, the basic peptide were able to be detected with the reagent for detection at its final concentrations in the mixed solution of 0.1 to 5% (or final concentrations of the contained denatured BSA of 0.005 to 0.25 w/v %).

Example 8

Evaluation of Detection Ability in Detection of Denatured BSA Solution for Neutral and Acidic Peptides 1. Experimental Procedures
(1) Preparation of Solution of Denatured BSA as Reagent for Detection The heat-denatured BSA solution was prepared in the similar manner as Example 1.

(2) Preparation of Sample Containing Peptide of Interest

Besides a basic peptide, to be studied for comparison, a neutral peptide Fibrinogen a (SEQ ID NO: 6; Biological Co.) and acidic peptides C3f (SEQ ID NO: 7; Biologica Co.) and Factor XIII (SEQ ID NO: 8; Biologica Co.) were prepared. These peptides were dissolved in ultrapure water to prepare samples containing respective peptides (1.0 mg/ml).

(3) Preparation of Mixed Solution of Reagent for Detection and Sample

The denatured BSA solution prepared in the above (1) (50 µl) was mixed with the respective samples prepared in (2) followed by addition of ultrapure water to prepare a total volume of 250 µl of mixed solutions containing the respective peptides. In the preparation, the sample was mixed with the heat-denatured BSA solution so as to obtain a final concentration of the respective peptides in the mixed solutions of 0 to 80 µM.

(4) Measurement of Absorbance of Mixed Solution

The thus-prepared mixed solutions were measured for OD550 in the similar manner as Example 1. The results are shown in FIGS. 7-1 to 7-4.

2. Results

Figures 1, 7:
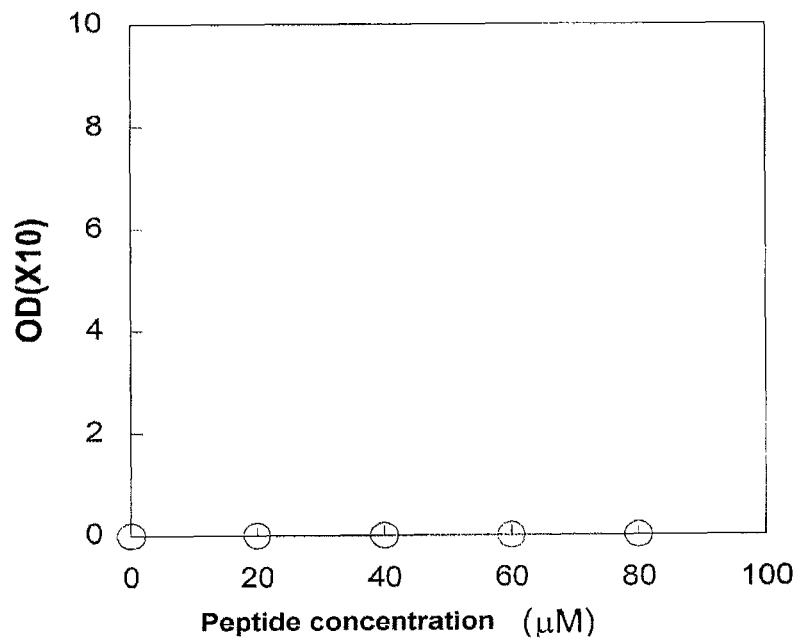
Figures 2, 7:
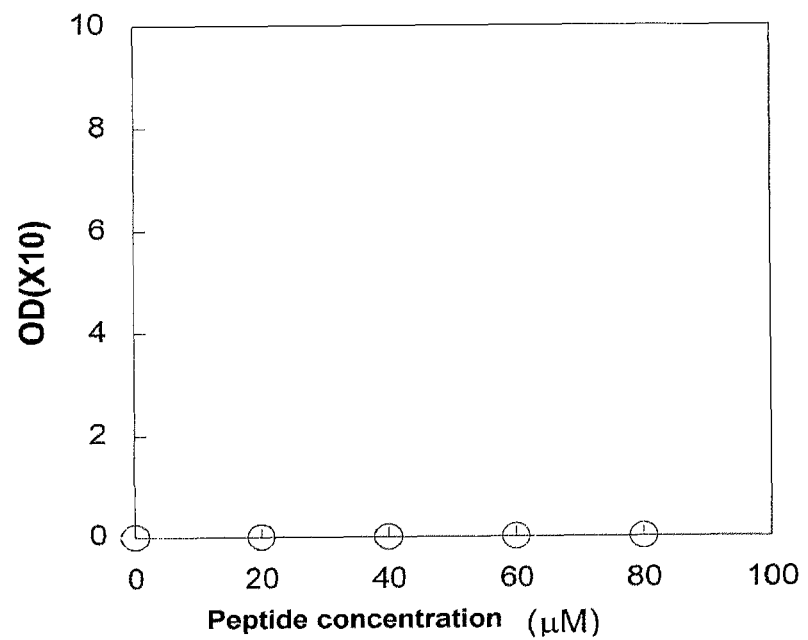
Figures 3, 7:
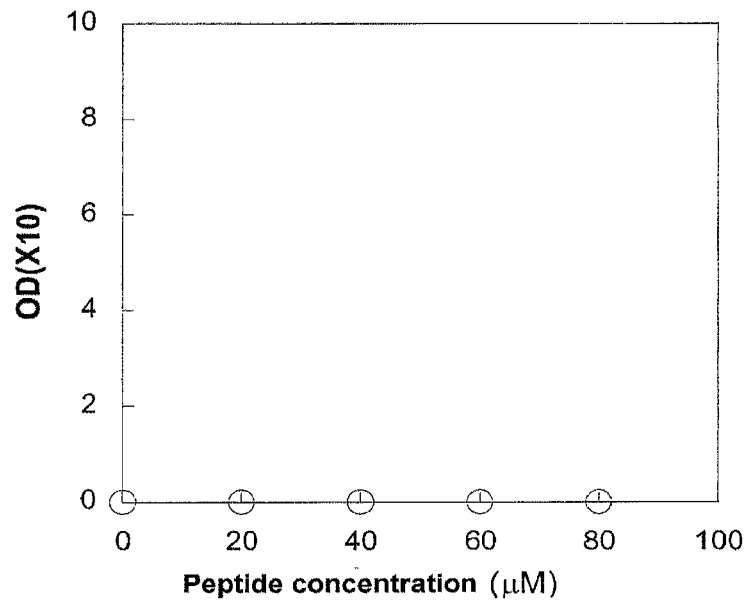
Figures 4, 7:
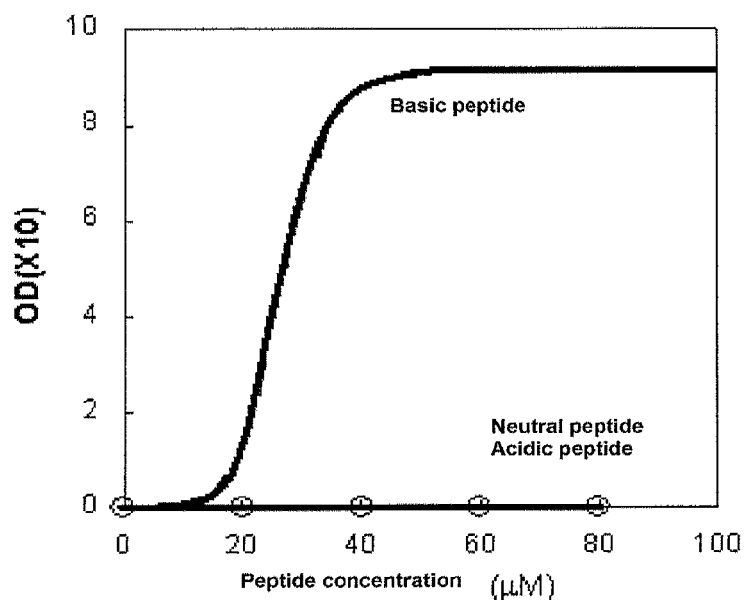

There was no change in OD550 when the neutral peptide Fibrinogen α was used (see FIG. 7-1). This may be because that heat-denatured BSA did not bind to Fibrinogen a or because the BSA dissociated from the peptide immediately after binding.

There was no change in OD550 when the acidic peptide C3f was used (see FIG. 7-2) or when Factor XIII was used (see FIG. 7-3). Again, these may be because that heat-denatured BSA did not bind to C3f or Factor XIII, or because that the BSA dissociated from the C3f or Factor XIII immediately after binding.

The plots for the above results were superimposed to that for the result of detection of the basic peptide in Example 1, as shown in FIG. 7-4. This plot clearly demonstrates that the present method is highly specific to basic peptides in detection without ability in detection for acidic and neutral peptides.

Example 9

Evaluation of Peptide Concentration Limit as Limit of Detection (LoD) in Peptide Detection Using Heat-Denatured BSA Solution 1. Experimental Procedures
(1) Preparation of Solution of Denatured BSA as Reagent for Detection The heat-denatured BSA solution was prepared in the similar manner as Example 1.

(2) Preparation of Sample Containing Basic Peptide of Interest

The sample containing the basic peptide was prepared in the similar manner as Example 6.

(3) Preparation of Mixed Solution of Reagent for Detection and Sample

The denatured BSA solution prepared in the above (1) (600 µl) was mixed with the sample prepared in (2) followed by addition of ultrapure water to prepare a total amount of 3 ml of mixed solution (final concentration of heat-denatured BSA: 0.2 w/v %). In the preparation, the sample was mixed with the heat-denatured BSA solution so as to obtain a final concentration of the partial ACTH peptide in the mixed solution of 0 to 1.6 µM.

Figure 8:
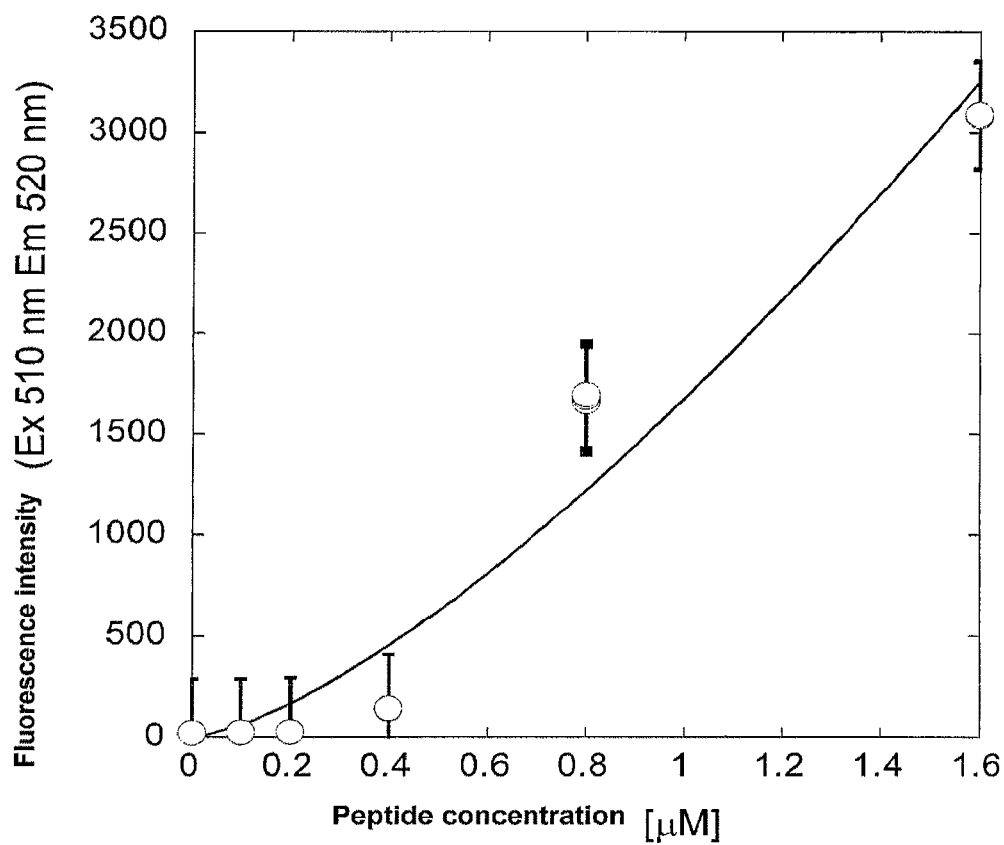
FIG. 8 is a plot of varied concentrations of a peptide versus fluorescence intensities of a mixed solution of the present reagent containing heat-denatured BSA and a sample containing a partial ACTH peptide.
Figure 9:
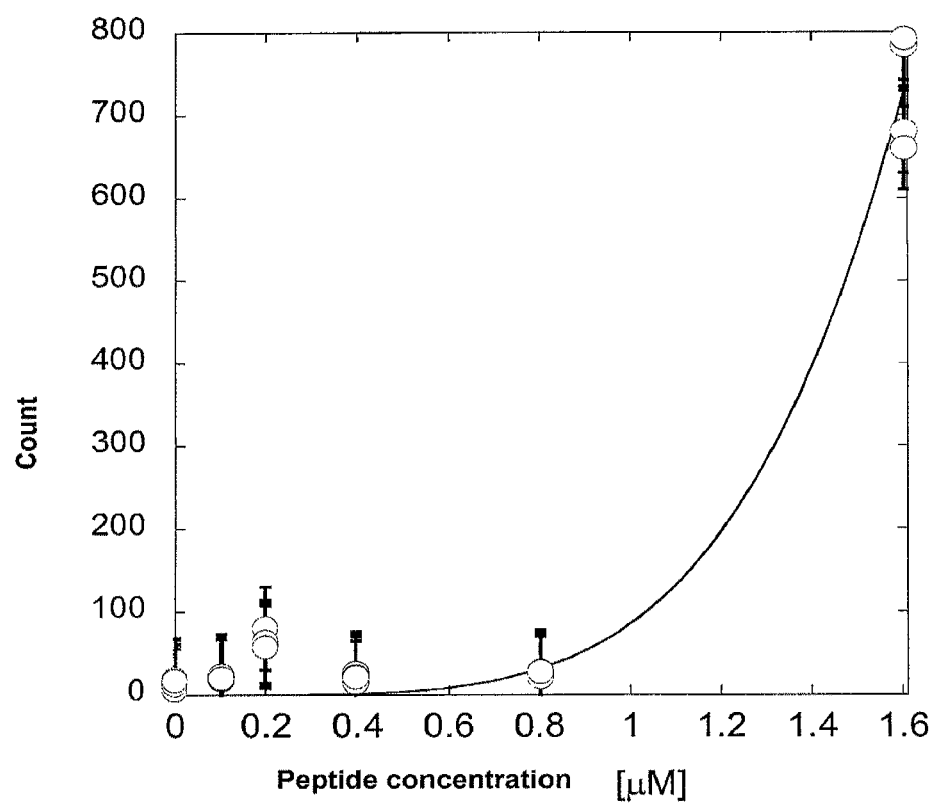
FIG. 9 is a plot of varied concentrations of a peptide versus the number of aggregates in a mixed solution for the mixed solution of the present reagent containing heat-denatured BSA and a sample containing a partial ACTH peptide.

(4) Measurement of Fluorescence Intensity and Counting of the Number of Aggregates by Microscopy of Mixed Solution The mixed solution prepared as above was divided into two aliquots. One of the aliquots was subjected to fluorometry with a spectrofluorometer F-7000 (Hitachi High-Technologies Corporation) at fluorescence intensity at 520 nm with excitation wavelength of 510 nm. The results are shown in FIG. 8. The obtained results were subjected to Hill plot analysis with KaleidaGraph (HULINKS, Inc.) to evaluate the peptide concentration limit as limit of detection (LoD). The other aliquot was subjected to microscopy with a microscope (×400, Olympus), that is, the aliquot was injected dropwise into a Plankton Counting Chamber (Matsunami Glass Ind., Ltd.) on the microscope stage and particles of aggregates present in a field of 843 µl×843 µl were counted. The results are shown in FIG. 9. The obtained results were subjected to Hill plot analysis with KaleidaGraph (HULINKS, Inc.) to evaluate the peptide concentration limit (LoD).

2. Results

FIG. 8 shows that when the peptide concentration was in the order of hundreds of nano molars (nM), the fluorescence intensity was increased in a concentration dependent manner of the basic peptide. The fluorescence intensity measured and the concentration of the basic peptide were obeyed a law described by the Hill equation.

FIG. 9 shows that the number counted microscopically of the aggregate particles was increased in a manner dependent on the concentration of the basic peptide. The counted number and the concentration of the basic peptide were obeyed a law described by the Hill equation.

Thus, the present method can be used for detection of the presence of and quantification of the concentration of the basic peptide of interest even when the concentration of the peptide is in an order of hundreds of nM.

Example 10

Evaluation of Ability in Detection for Basic Peptide in Serum-Based Sample

1. Experimental Procedures
(1) Preparation of Solution of Denatured BSA as Reagent for Detection The heat-denatured BSA solution was prepared in the similar manner as Example 1.

(2) Preparation of Serum-Based Solution Containing Basic Peptide of Interest

A partial ACTH peptide consisting of the amino acids of positions 1 to 24 of ACTH (Biologica Co.) was used as the basic peptide of interest. The peptide was dissolved in ultrapure water and mixed with serum collected from a healthy volunteer in USA (female, 16 years old) (SUNFCO) to prepare the serum-based sample containing the basic peptide of interest. The serum-based samples were prepared so as to adjust the final concentrations of the partial ACTH peptide and serum as shown in (3) below.

(3) Preparation of Mixed Solution of Reagent for Detection and Sample

The denatured BSA solution prepared in the above (1) (50 µl) was mixed with the sample prepared in (2) followed by addition of ultrapure water to prepare a total volume of 250 µl of mixed solution containing serum (hereinafter referred to as "serum-based solution"). In the preparation, the serum-based sample was mixed so as to adjust a final concentration of the partial ACTH peptide of to 0 to 80 µM and adjust a final concentration of serum of to an equivalent to 100-fold dilution in the mixed solution. For a control, a mixed solution was also prepared without serum (hereinafter referred to as "control solution").

(4) Measurement of Absorbance of Mixed Solutions

Figure 10:
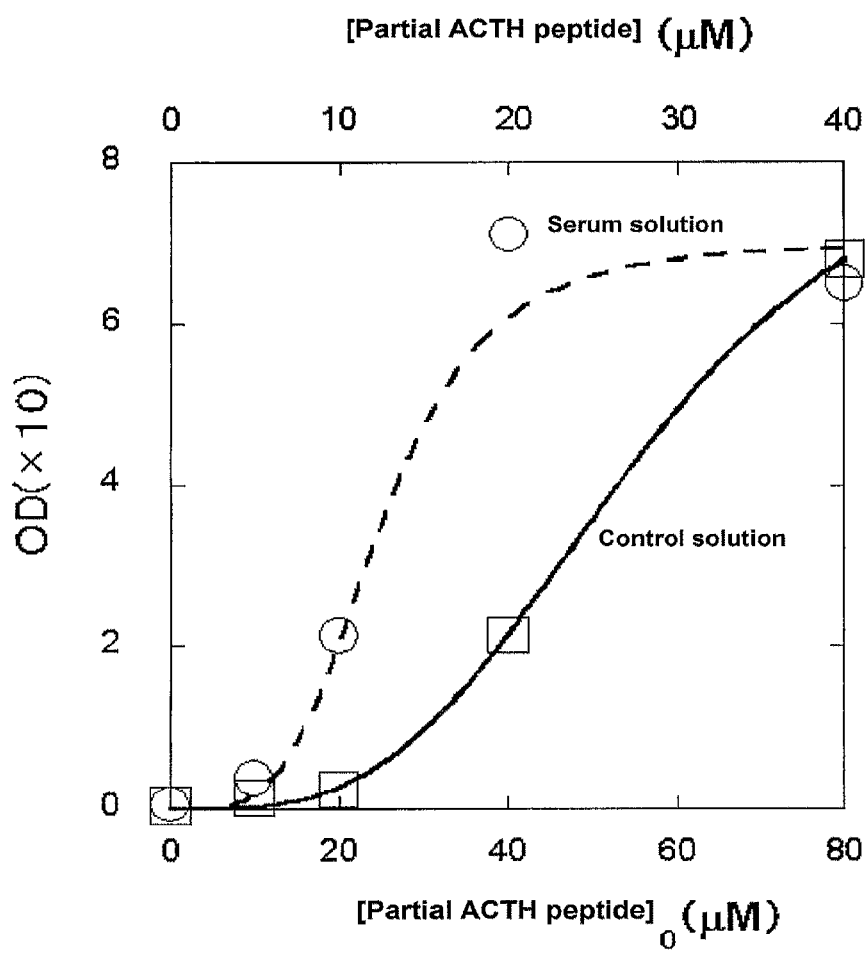
FIG. 10 is a plot of varied concentrations of a peptide versus values of OD measured when a partial ACTH peptide is detected in a sample with or without serum using the present reagent containing heat-denatured BSA.

The thus-prepared mixed solutions were measured for absorbance at the wavelength of 550 nm (OD550) with a spectrophotometer UV-2500PC (Shimadzu Corporation). The results are shown in FIG. 10. The obtained results were subjected to Hill plot analysis with KaleidaGraph (HULINKS, Inc.) to calculate the values of Kd and the Hill coefficient of heat-denatured BSA, HSA concentration ($C_{HSA}$), dissociation constants (Ki values) of HSA and ACTH. The values are shown in Table 7.

TABLE 7

| Reagent | Kd (µM) | Hill coefficient n | $C_{HSA}$ (µM) | Ki (µM) |
|---|---|---|---|---|
| Control solution (without serum) | 25 | 4 | 0 | 50 |
| Serum solution | 29 | 3.4 | 47 | 52 |

2. Results

FIG. 10 demonstrates that the basic peptide is able to be detected in a pure sample which contained the basic peptide of interest as in Examples 1 to 9 as well as in the serum-based samples which is the actually same as sera collected from medical examinees.

It is found from FIG. 10 that the concentration of the partial ACTH peptide in the control solution corresponding to a certain OD value is about two times higher than the concentration of the partial ACTH peptide in the serum-based sample solution. This difference is attributed to an effect of competitive inhibition by HSA in serum. In the serum-based solution, the dissociation constant between the HSA in serum and the partial ACTH peptide needs to be considered. The relation between the absorbance and the concentration of the basic peptide is confirmed to follow the following Hill equation.

$$OD = (\text{peptide concentration})^n / [(\text{peptide concentration})^n + [Kd \times (1 + C_{HSA}/Ki)]^n]$$

(wherein, Kd is the dissociation constant between the partial ACTH peptide and heat-denatured BSA, $C_{HSA}$ is the concentration of HSA, Ki is the dissociation constant between the partial ACTH peptide and HSA, and n is the Hill coefficient).

Table 7 shows that the values of Kd and the Hill coefficient, n, which are the factors associated with the detection activity of the detection reagent itself are consistent between the control solution and the serum solution. There is, in contrast, no correlation in the values of $C_{HSA}$ between these solutions. From these results, it is apparent that the detection activity of the reagent for detection was not decreased, but HSA in serum captured some of the partial ACTH peptides to actually decrease the amount of free peptides in the solutions.

The above results show that the present method ensures detection and quantification of the concentration of the basic peptide contained in living specimens.

In order to enhance the sensitivity in detection of basic peptides, the present method may also comprise the step of concentrating the peptides in advance. Such method is shown in the next example.

Example 11

Concentration of Basic Peptide in Serum-Containing Specimen and Detection of Concentrated Basic Peptide 1. Experimental Procedures
(1) Preparation of Solution of Denatured BSA as Reagent for Detection The heat-denatured BSA solution was prepared in the similar manner as Example 1.

(2) Preparation of Actual Serum Solution Containing Basic Peptide of Interest

A partial ACTH peptide consisting of amino acids of positions 1 to 24 of ACTH (Biologica Co.) was used as the basic peptide of interest. The peptide was dissolved in ultrapure water and mixed with serum of a healthy USA subject (female, 16 years old) (SUNFCO) to prepare an actual serum sample containing the basic peptide of interest. The sample was prepared so as to obtain the concentrations of the partial ACTH peptide and serum as shown in (3) below.

(3) Preparation of sample solution containing concentrated basic peptide of interest. A glycerol solution (Agilent technologies; 6 ml) and an OFFGEL Buffer solution (Agilent technologies; 600 µl) were mixed followed by addition of ultrapure water to prepare a total volume of 50 ml of peptide buffer solution (×1.25), the pH of which is 3-10. This solution was mixed with the sample of the above (2) to prepare a peptide buffer solution (×1) with the concentration of 20 µM of the partial ACTH peptide and the concentration equivalent to 1000-fold dilution of serum. This solution was fractionated with using a High Resolution IPG gel for fraction whose pH is pH 3-10 on the OFFGEL fractionator (Agilent Technologies). The fraction containing the partial ACTH peptide (solution flanking to cathode) was then collected and transferred to 100 µl of ultrapure water to obtain a concentrated basic peptide sample.

(4) Preparation of Mixed Solution of Reagent for Detection and Sample

The heat-denatured BSA solution prepared in the above (1) (50 µl) was mixed with the sample prepared in (3) followed by addition of a MES-HCl buffer (pH 5.0) and ultrapure water to obtain a total volume of 250 µl (final concentration of MES: 50 µM) and pH was adjusted to prepare a mixed solution. A comparative mixed solution was prepared without the heat-denatured BSA solution.

(5) Measurement of Absorbance of Mixed Solution

The thus-prepared mixed solutions were measured for absorbance at the wavelength of 550 nm (OD550) in a spectrophotometer UV-2500PC (Shimadzu Corporation). The results are shown in Table 8.

TABLE 8

| Heat-denatured BSA | OD550 |
|---|---|
| Yes | 0.03 |
| No | 4.36 |

2. Results

As increase in turbidity was observed for the sample containing the heat-denatured BSA, it was found that the partial ACTH peptide could be detected in the solution after OFFGEL fractionation with the reagent for detection of the present invention.

Thus, the present method ensures detection of a trace amount of a basic peptide in actual specimens preceded by concentration of the basic peptide with an OFFGEL fractionator.

The present application relates to Japanese Patent Application No. 2009-280935 filed on Dec. 10, 2009, whose claims, specification, drawings and abstract are incorporated herein by reference.

What is claimed is:

1. A method for detection of a basic peptide comprising the steps of:
   (1) mixing a sample suspected to contain the basic peptide and a reagent containing a heat-denatured albumin to form a complex between the basic peptide and the heat-denatured albumin; and
   (2) detecting a turbidness of a mixture obtained in the step (1) wherein an increase in turbidness is indicative of the presence of said basic peptide.

2. The method according to claim 1, wherein a final concentration of the denatured albumin in the mixture is 0.2 to 0.6 w/v %.

3. The method according to claim 1, wherein the step (2) is a step of irradiating the mixture with light to obtain optical information.

4. The method according to claim 3, wherein the optical information is an absorbance.

* * * * *

SEQUENCE LISTING

```
<160> NUMBER OF SEQ ID NOS: 8

<210> SEQ ID NO 1
<211> LENGTH: 24
<212> TYPE: PRT
<213> ORGANISM: Homo sapiens

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 2
<211> LENGTH: 13
<212> TYPE: PRT
<213> ORGANISM: Homo sapiens

<400> SEQUENCE: 2

Tyr Gly Gly Phe Leu Arg Arg Ile Arg Pro Lys Leu Lys
1               5                   10

<210> SEQ ID NO 3
<211> LENGTH: 16
<212> TYPE: PRT
<213> ORGANISM: Homo sapiens

<400> SEQUENCE: 3

Tyr Gly Gly Phe Met Thr Ser Glu Lys Ser Gln Thr Pro Leu Val Thr
1               5                   10                  15

<210> SEQ ID NO 4
<211> LENGTH: 19
<212> TYPE: PRT
<213> ORGANISM: Homo sapiens

<400> SEQUENCE: 4

His Asn Leu Gly His Gly His Lys His Glu Arg Asp Gln Gly His Gly
1               5                   10                  15

His Gln Arg

<210> SEQ ID NO 5
<211> LENGTH: 32
<212> TYPE: PRT
<213> ORGANISM: Homo sapiens

<400> SEQUENCE: 5

Gly Glu Ser Arg Asn Arg Asn Val His Ser Gly Ser Thr Phe Phe Lys
1               5                   10                  15

Tyr Tyr Leu Gln Gly Ala Lys Ile Pro Lys Pro Glu Ala Ser Phe Ser
            20                  25                  30

<210> SEQ ID NO 6
<211> LENGTH: 25
<212> TYPE: PRT
<213> ORGANISM: Homo sapiens
```

```
<400> SEQUENCE: 6

Asp Glu Ala Gly Ser Glu Ala Asp His Glu Gly Thr His Ser Thr Lys
1               5                   10                  15

Arg Gly His Ala Lys Ser Arg Pro Val
            20                  25

<210> SEQ ID NO 7
<211> LENGTH: 8
<212> TYPE: PRT
<213> ORGANISM: Homo sapiens

<400> SEQUENCE: 7

His Trp Glu Ser Ala Ser Leu Leu
1               5

<210> SEQ ID NO 8
<211> LENGTH: 25
<212> TYPE: PRT
<213> ORGANISM: Homo sapiens

<400> SEQUENCE: 8

Ala Val Pro Pro Asn Asn Ser Asn Ala Ala Glu Asp Asp Leu Pro Thr
1               5                   10                  15

Val Glu Leu Gln Gly Val Val Pro Arg
            20                  25
```